United States Patent [19]
Bruza

[11] Patent Number: 5,028,712
[45] Date of Patent: Jul. 2, 1991

[54] CYCLOBUTARENE KETOANHYDRIDE AND KETOCARBOXY MONOMERIC AND POLYMER COMPOSITIONS

[75] Inventor: Kenneth J. Bruza, Midland, Mich.

[73] Assignee: The Dow Chemical Company, Midland, Mich.

[21] Appl. No.: 528,271

[22] Filed: May 24, 1990

Related U.S. Application Data

[63] Continuation of Ser. No. 46,368, May 6, 1987, abandoned.

[51] Int. Cl.$^5$ .................. C07D 213/00; C07D 213/62; C08G 2/18; C08G 16/00
[52] U.S. Cl. .................................... 546/261; 546/260
[58] Field of Search ............................... 546/260, 261

[56] References Cited

U.S. PATENT DOCUMENTS 4,540,763  9/1985  Kirchhoff ............................ 528/271

FOREIGN PATENT DOCUMENTS 0175647  3/1986  European Pat. Off. .

OTHER PUBLICATIONS

Pearson et al., *Synthesis*, pp. 533–542 (1972), "Friedel–Crafts Acylations With Little or No Catalyst".
Morley, *J. Chem. Soc. Perkin II*, pp. 601–605, "Aromatic Acylations Catalysed by Metal Oxides" (1977).
Morley, *Synthesis*, pp. 54–55 (1977), "Benzoylation of Halobenzenes Catalysed by Iron (III) Sulphate".
Lloyd et al., *Tetrahedron*, vol. 21, pp. 245–254, (1965), "The Electrophilic Substitution of Benzocyclobutene-II".
Jensen et al., *J. Org. Chem.*, vol. 25, pp. 640–641 (1960), "Unsaturated Four-Membered Ring Compounds. III. The Reactivity of Benzycyclobutene Toward Electrophilic Substitution".
Chiusoli et al., *Transition Met. Chem.* 2, 270–272 (1977), "Synthesis of Ketones from Aroyl Chlorides an"d Nickel (O) Complexes.
Tsukervanik et al., Uzbek. Khim. Zhur No. 2, pp. 60–62 (1961) abstract from *Chem. Abstracts;* vol. 55, (1961) col. 272206, "Acylation of Arommatic Compounds in the Presence of Metals".
Tsukervanik, Daklady Akad. Nauk Uzbek. SSR No. 4, pp. 36–39 (1959) abstract from Chem. Abstracts, vol. 54 (1960) col. 10816–17, "Iron Powder as an Alkylation and Acylation Catalyst".

*Primary Examiner*—John Kight, III
*Assistant Examiner*—P. Hampton Hightower
*Attorney, Agent, or Firm*—Charles J. Enright

[57] ABSTRACT

The invention comprises cyclobutarene ketoanhydride monomers and the process for preparing them, and cyclobutarene ketocarboxy monomers. The monomers can be copolymerized with suitable difunctional monomers and subsequently processed to prepare highly crosslinked structures. The monomers can also be used to endcap oligomers with the cyclobutarene functionality. The endcapped oligomer can subsequently be processed to prepare a highly crosslinked network.

24 Claims, No Drawings

CYCLOBUTARENE KETOANHYDRIDE AND KETOCARBOXY MONOMERIC AND POLYMER COMPOSITIONS

This is a continuation of application Ser. No. 046,368 filed May 6, 1987, now abandoned.

BACKGROUND OF THE INVENTION

This invention relates to improved monomeric and polymeric compositions derived from cyclobutarenes and the processes for preparing them.

Polymeric compositions derived from biscyclobutarene monomers are disclosed in U.S. Pat. No. 4,540,763. They are prepared by subjecting biscyclobutarene monomers to temperatures sufficient to polymerize the monomers. These compositions exhibit excellent thermal stability at high temperatures, good chemical resistance to most industrial solvents, and low solubility in water. These properties are highly desirable for applications in the electronics and aerospace industries, as well as for any other application where thermoset resins exhibiting outstanding physical and mechanical properties are required.

Thermoset resins are monomeric and polymeric compositions which can solidify irreversibly upon heating. They are useful in many engineering applications. For example, they are useful as coatings, structural laminates, adhesives, films, and composites. Typical thermoset resins exhibiting properties which encourage their use as engineering materials include polyesters, polycarbonates, polyamides, polyimides, and epoxy resins.

Unfortunately, conventional thermoset resins do not exhibit the thermal stability, chemical resistance, and low water solubility of the polymeric compositions of U.S. Pat. No. 4,540,763 prepared from biscyclobutarene monomers. Therefore, it would be desirable to provide improved thermoset resins derived from cyclobutarenes that exhibit the properties required for demanding applications in the electronics and aerospace industries, as well as other industries where high performance is required.

SUMMARY OF THE INVENTION

In one aspect, the invention represents two monomer compositions and the process for preparing the first monomer composition.

The first monomers are represented by the formula:

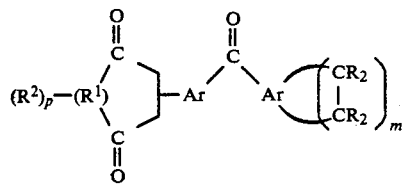

wherein

Ar is an aryl moiety or a heterocyclic moiety;

R is separately and independently in each occurrence a hydrogen atom, an electron donating moiety or an electron withdrawing moiety;

$R^1$ is an oxygen atom, a nitrogen atom, or a sulphur atom;

$R^2$ is a hydrogen atom, an alkyl moiety having less than 10 carbon atoms, an aryl moiety, or a heterocyclic moiety;

m is an integer of 1 or 2; and p is an integer of zero or 1 provided that p is 1 only when $R^1$ is a nitrogen atom.

The process for preparing the first monomers comprises the step of reacting a cyclobutarene with an anhydride-substituted aromatic acid halide in the presence of a reaction catalyst capable of either accepting a pair of electrons or donating a proton during the reaction.

The second monomers are represented by the formula:

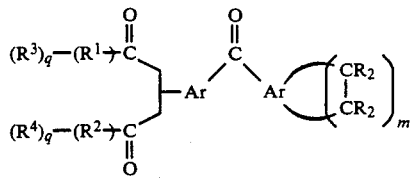

wherein

Ar, R and m have the same definition as provided for the first monomers;

$R^1$ and $R^2$ are separately and independently in each occurrence a nitrogen atom, an oxygen atom, or a sulphur atom;

$R^3$ and $R^4$ are separately and independently in each occurrence a hydrogen atom, an alkyl moiety having less than 10 carbon atoms, an aryl moiety, or a heterocyclic moiety; and q is an integer of 1 or 2 provided that q is 2 only when $R^1$ or $R^2$ is a nitrogen atom.

In another aspect, the invention is a process for preparing a copolymer from any monomer of this invention comprising the step of subjecting the monomer and a difunctional monomer that can undergo at least two condensation reactions to condensation polymerization conditions.

The invention is also a process for preparing an oligomer endcapped with a cyclobutarene moiety comprising the step of subjecting a difunctional oligomer that can undergo at least two condensation reactions and any monomer of this invention to condensation polymerization conditions.

In yet another aspect, the invention is a process for preparing a crosslinked network for the copolymers or endcapped oligomers prepared from the processes of this invention, comprising the step of subjecting the copolymer or endcapped oligomer to ring scission polymerization conditions.

In a final aspect, the invention is a process for preparing a homopolymer from any first monomer of this invention, comprising the step of subjecting the monomer to ring scission polymerization conditions.

The monomer and polymer compositions of this invention provide a family of improved thermoset resins. These resins can be processed to prepare engineering materials for the electronics and aerospace industries. They possess outstanding mechanical, physical, and electrical properties, as well as good chemical resistance and thermal stability at high temperatures. They can also be blended or alloyed with conventional thermoset resins to prepare resins with improved properties for any industry where high performance is required.

DETAILED DESCRIPTION OF THE INVENTION

The monomers of this invention have the following formula:

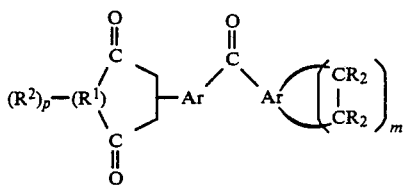

wherein

Ar is an aryl moiety or a heterocyclic moiety;

R is separately and independently in each occurrence a hydrogen atom, an electron donating moiety or an electron withdrawing moiety;

$R^1$ is an oxygen atom, a nitrogen atom, or a sulphur atom;

$R^2$ is a hydrogen atom, an alkyl moiety having less than 10 carbon atoms, an aryl moiety, or a heterocyclic moiety;

m is an integer of 1 to 2;

p is an integer of zero or 1 provided that p is 1 only when $R^1$ is a nitrogen atom.

An aryl moiety is an aromatic compound containing (4N+2)n electrons as described in Morrison & Boyd, *Organic Chemistry*, 3rd ed., 1973. Aryl moieties include benzene, naphthalene, phenanthrene, anthracene, and two or more aromatic moieties bridged by alkylene, cycloalkylene, oxygen, nitrogen, sulfoxide, sulfone, or carbonyl moieties. Also included are substituted aromatic compounds. The preferred aryl moieties are benzene and naphthalene.

A heterocyclic moiety is an aryl moiety having atoms other than carbon atoms in its nucleus. Heterocyclic moieties include pyridine and picoline.

Electron-donating moieties are molecular or nuclear gorups which donate electrons more than a hydrogen atom would if accompanying the same site. Electron-withdrawing moieties are groups which more redily withdraw an electron relative to a hydrogen atom. Examples of suitable electron-withdrawing moieties include $-NO_2$, $-CN$, Br, I, Cl, F, $-CO_2H$, $-CO_2R$,

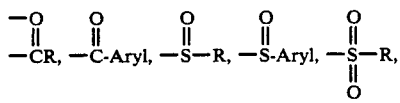

and aryl. Examples of suitable electron-donating moieties include alkyl, aryl, alkoxy, aryloxy, hydrocarbyl, hydrocarbyloxy, hydrocarbylthio, $-OH$, $-OR$, $-NH_2$, $-NHR$, $-NR_2$. Hydrocarbyl refers to any organic moiety containing only carbon and hydrogen atoms; hydrocarbyloxy refers to such organic moieties which further contain a hydroxyl moiety; and hydrocarbylthio refers to organic moieties which further contain a thiol moiety.

Separately and independently in each occurrence means that each R can be different in each occurrence.

The monomers represented by the formula above will be referred to as cyclobutarene ketoanhydride monomers. The most preferred cyclobutarene ketoanhydride monomer has the following formula:

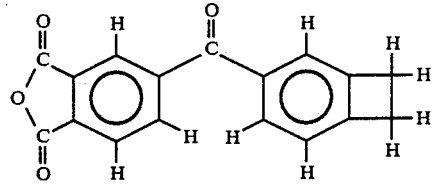

The monomers of this invention also have the following formula:

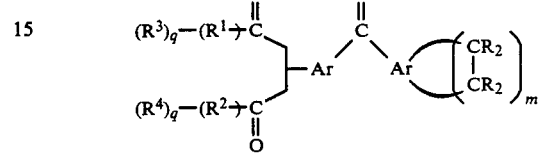

wherein

Ar, R and m have the same definition as provided for the cyclobutarene ketoanhydride monomers;

$R^1$ and $R^2$ are separately and independently in each occurrence a nitrogen atom, an oxygen atom, or a sulphur atom;

$R^3$ and $r^4$ are separately and independently in each occurrence a hydrogen atom, an alkyl moiety having less than 10 carbon atoms, an aryl moiety, or a heterocyclic moiety; and q is an integer of 1 or 2 provided that q is 2 only when $R^1$ or $R^2$ is a nitrogen atom.

These monomers will be referred to as cyclobutarene ketocarboxy monomers. A preferred cyclobutarene ketocarboxy monomer has the following formula:

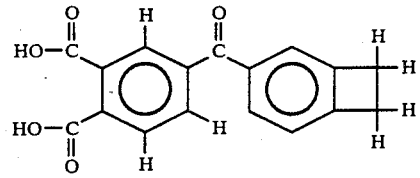

This monomer will be referred to as a cyclobutarene ketocarboxylic acid monomer. Another preferred cyclobutarene ketocarboxy monomer has the following formula:

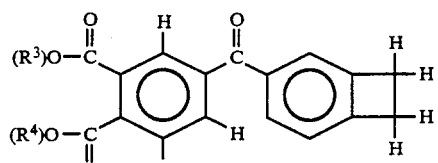

wherein $R^3$ and $R^4$ are both identical alkyl moieties having less than 10 carbon atoms.

This monomer will be referred to as an cyclobutarene ketocarboxylic ester monomer. The most preferred cyclobutarene ketocarboxy ester monomer occurs when $R^3$ and $R^4$ are ethyl.

The cyclobutarene ketoanhydride monomers of this invention can be prepared by reacting a cyclobutarene with an cid halide in the presence of a suitable reaction catalyst. A cyclobutarene refers to a compound containing at least one aromatic ring to which is fused one or more cyclobutane rings. The acid halide is an anhydride-substituted aromatic acid halide of the formula:

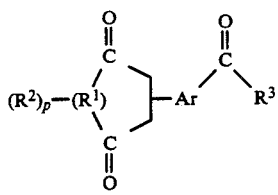

wherein

Ar, $R^1$, $R^2$, and p have the same definition as provided for the cyclobutarene ketoanhydride monomers; and $R^3$ is a chlorine atom, bromine atom, or iodine atom.

The most preferred cyclobutarene is benzocyclobutene. The most preferred acid halide has the formula:

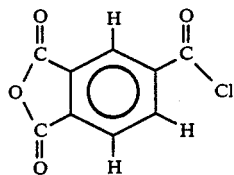

This acid halide is commonly referred to as trimellitic anhydride acid chloride. The reaction of benzocyclobutene with trimellitic anhydride acid chloride will produce the most preferred cyclobutarene ketoanhydride monomer.

Suitable reaction catalysts include compounds which function as Lewis acids; such as tin (IV) chloride, tin (II) chloride, antimony (III) chloride, antimony (V) chloride, any aluminum salt or oxide, any iron salt or oxide, iron metal, any zinc oxide, and zinc metal; strong protic acids such as sulfuric acid, polyphosphoric acid, and trifluoroacetic acid; and certain organometallic compounds such as organic complexes of iron and trifluoroacetic anhydride. Compounds which function as Lewis acids are those compounds having the ability to accept a pair of electrons from another compound. A protic acid is a compound that will donate a proton during a chemical reaction. The preferred reaction catalysts are iron (III) oxide, and zinc oxide. The most preferred reaction catalyst is iron (III) oxide.

As disclosed in U.S. Pat. No. 4,570,011, cyclobutarenes can be prepared by dissolving an ortho alkyl halomethyl aromatic hydrocarbon, such as ortho methylchloromethylbenzene, in an inert solvent, and then pyrolyzing the solution under suitable reaction conditions. Anhydride-substituted aromatic acid halides useful in this invention can be prepared by reacting 1 equivalent of 1,2,4-benzenetricarboxylic anhydride with 2 equivalents of a thionyl halide or a phosphorous trihalide. The reaction mixture is heated to reflux and maintained at reflux for about 1 hour. After the reaction, the mixture is cooled to room temperature. The excess thionyl halide or phosphorous trihalide can then be physically separated from the acid halide.

The molar ratio of the cyclobutarene to the acid halide required for the reaction can range from about 5:4 to about 40:4. The preferred molar ratio can range from about 6:4 to about 12:4. The most preferred molar ratio is about 6:4. The required molar ratio of the acid halide to the reaction catalyst can range from about 5 to about 10,000. The preferred ratio can range from about 10 to about 500.

The temperature required for the reaction can range from about 100° C. to about 180° C., with a preferred range from about 135° C. to about 150° C. Generally, as the reaction temperature increases, the time required for the reaction decreases. The time required to reach a yield of the cyclobutarene ketoanhydride monomer of between 30 weight percent and 50 weight percent can range from about 4 hours to about 24 hours. Yield is defined as the weight percent of reactants that form the cyclobutarene ketoanhydride monomer. Preferably, the reactants are stirred vigorously during the reaction.

After the reaction, the cyclobutarene ketoanhydride monomer must be separated from the reaction mixture. One method of separation involves cooling the mixture to room temperature and adding an aliphatic hydrocarbon solvent, such as heptane or hexane, to the reaction mixture in an amount sufficient to at least double its volume. The diluted mixture is heated to reflux and the solvent is subsequently decanted. When the mixture cools, the monomer will crystallize. The monomer can then be physically separated from the remaining mixture by filtration.

In a preferred embodiment of this invention, the reaction catalyst is separated and hydrochloric acid liberated during the reaction is neutralized before the aliphatic hydrocarbon solvent is added. One method involves contacting the reaction mixture with chloroform and washing with aqueous base to neutralize the acid component. After drying the chloroform solution, the cyclobutarene ketoanhydride can be obtained by evaporation of the chloroform.

The cyclobutarene ketocarboxylic acid monomers of this invention can be prepared by first reacting an cyclobutarene ketoanhydride monomer with a strong base to form an intermediate. The intermediate can then be reacted with a protic acid to form the desired monomer. Examples of strong bases are aqueous sodium hydroxide, potassium hydroxide, calcium hydroxide, and magnesium hydroxide. The preferred base is sodium hydroxide. Examples of suitable protic acids are hydrochloric acid, sulfuric acid, nitric acid, phosphoric acid, acetic acid and para-toluene sulfonic acid. The preferred protic acids are hydrochloric acid and para-toluene sulfonic acid.

The molar ratio of the base to the cyclobutarene ketoanhydride monomer required for the reaction to form the intermediate can range from about 2 to about 50. The preferred ratio is from about 5 to about 10. The required temperature can range from about 20° C. to about 100° C., with a preferred range from about 80° C. to about 100° C. The reaction time will vary with the temperature, and will range from about 1 hour to about 24 hours. Preferably, the reactants are stirred vigorously during the reaction.

The amount of acid required for the reaction of the intermediate to form the cyclobutarene ketocarboxylic acid monomer will vary with the amount of base added to form the intermediate. The acid is added in an amount sufficient to neutralize the reaction mixture to a pH ranging from about 2 to about 6. The required temperature ranges from about 5° C. to about 50° C., with a preferred range from about 5° C. to 20° C. The reaction time will range from about 5 minutes to about 30 minutes. Again, it is preferable to stir the reactants vigorously during the reaction.

The cyclobutarene ketocarboxylic acid monomer can easily be physically separated from the reaction mixture, such as for example by filtration.

The cyclobutarene ketocarboxylic ester monomers of this invention can be prepared by reacting an cyclobutarene ketoanhydride monomer with an alcohol in the presence of a protic acid. The alcohol can be any organic compound that contains at least one hydroxyl group, such as aliphatic alcohols, phenols, and substituted phenols. Generally, saturated aliphatic alcohols having less than 10 carbon atoms are preferred. The most preferred alcohol is ethanol. Suitable protic acids are those that are listed above for the preparation of the cyclobutarene ketocarboxylic acid monomers.

The required weight ratio of alcohol to monomer can range from about 3:1 to about 20:1, more preferably from about 3:1 to 8:1. The required molar ratio of monomer to protic acid can range from about 3:1 to 10:1, more preferably from about 4:1 to 5:1. The reactants are heated to rflux and maintained at reflux for a time period ranging froma bout 4 hours to 12 hours, depending on the reactivity of the alcohol and the molar ratio of monomer to protic acid.

The monomer can be separated from the reaction mixture by dissolving the mixture in chloroform and then washing the dissolved mixture with an aqueous base to preferentially remove excess acid. The monomer can then be physically separated from the remaining mixture by evaporation of the chloroform.

The cyclobutarene ketoanhydride monomers and the cyclobutarene ketocarboxy monomers of this invention can be copolymerized with one or more difunctional monomers that can undergo at least two condensation reactions. Copolymers such as polyesters, polyamides, and polyimides can be prepared by subjecting the monomers to condensation polymerization conditions. The terms "polymers" and "copolymers" refer to two or more mers bonded together. This includes dimers, oligomers, and prepolymers.

The term "condensation reaction" refers to a reaction in which a small molecule, most often water, is split out. The term "condensation polymerization" is used in its traditional sense and refers to a polymerization which proceeds via an organic condensation reaction. A typical condensation polymerization involves the esterification reaction of an organic acid and an organic base.

The process conditions sufficient to promote condensation polymerization are well known and are described in Sandler et al., *Polymer Syntheses* Vol. I, pp. 55-115 (Academic Press, Inc., 1974). Generally, equimolar amounts of a monomer of this invention and a suitable difunctional monomer can be diluted in an appropriate solvent, such as toluene or xylene, and stirred sufficiently to prepare a homogeneous reaction mixture. The mixture is then maintained at room temperature or heated to a temperature ranging up to 180° C. under a nitrogen atmosphere for about 4 to about 16 hours. The required process conditions will depend on the difunctional monomer selected, the copolymer desired, the reactivity of the mixture and the desired molecular weight of the prepared copolymer. During the polymerization, means must be provided in most instances to remove the condensation byproduct which splits out from the polymerization reaction.

The difunctional monomers that can undergo at least two condensation reactions include primary aromatic dimaines such as methylene dianiline, oxydianiline, phenylenediamine, diaminodiphenylsulphone, diaminodiphenylsulphide, and diaminodiphenylsulphoxide; secondary aromatic diamines such as N,N-dimethyl-1,4-diaminobenzene and N,N-dimethylmethylenedianiline; saturated aliphatic diols such as 1,6-hexane diol and 1,4-butane diol; diphenols such as bisphenol A, hydroquinone, and resorcinol; and dithiols such as ethanedithiol, 1,3-propanedithiol, and benzenedithiol. The preferred difunctional monomers are methylene dianiline; 1,4-butane diol; bisphenol A; and benzenedithiol.

A polyester can be prepared by subjecting any monomer of this invention and a saturated aliphatic diol to condensation polymerization conditions. As an example, the copolymerization of the most preferred cyclobutarene ketoanhydride monomer and 1,4-butanediol will form a polyester of the formula:

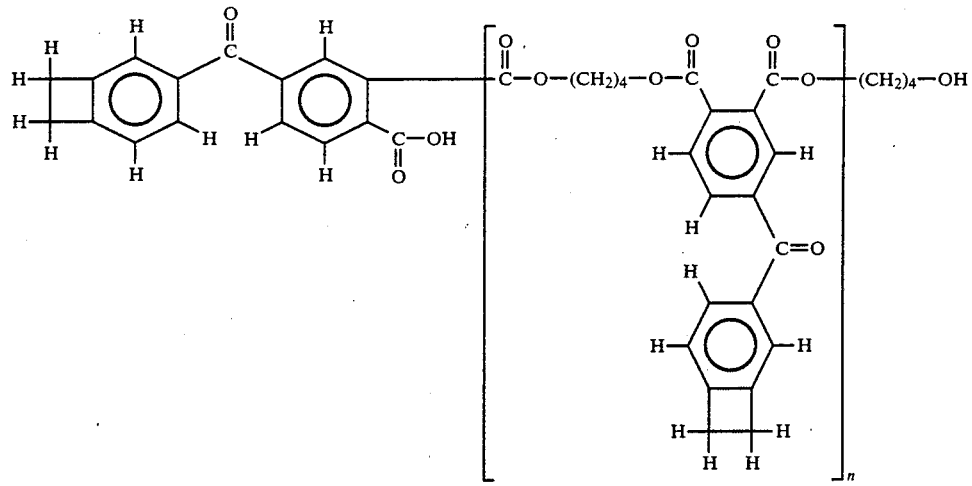

wherein n is an integer greater than or equal to 1.

A polyamide can be prepared by subjecting a monomer of this invention and either a primary aromatic diamine or a secondary aromatic diamine to condensation polymerization conditions. Preferably, a secondary aromatic diamine is used. As an example of this reaction, the copolymerization of the most preferred cyclobutarene ketoanhydride monomer and methylene dianiline will form a polyamide of the formula:

ployed ranges from about 5 mole precent to about 20 mole percent based on the total molar amount of monomer and oligomer in the reaction mixture.

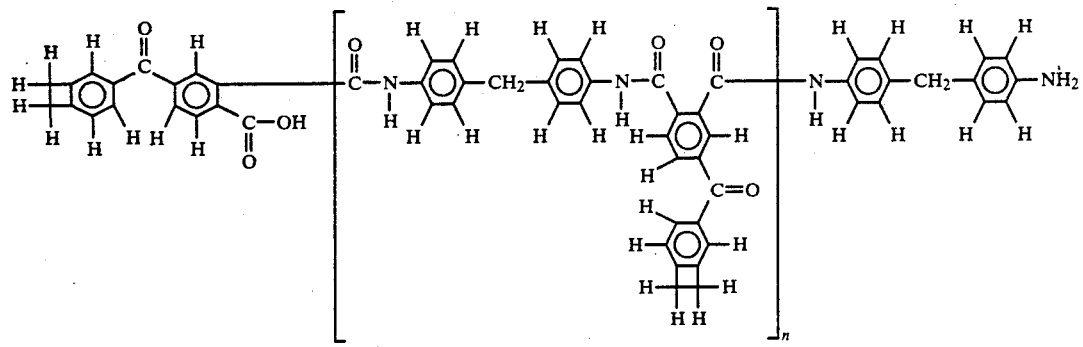

wherein n is an integer greater than or equal to 1.

In a preferred embodiment of this invention, difunctional oligomers that can undergo at least two condensation reactions such as polyester, polyamide, and polyimide oligomers are endcapped with either the cyclobutarene ketoanhydride monomers or the cyclobutarene ketocarboxy monomers. The term "difuntional oligomer" refers to a difunctional polymer of 2, 3, or 4

An endcapped polyester can be prepared by subjecting a polyester oligomer and a cyclobutarene monomer to suitable condensation polymerization conditions. As an example, the endcapping of a polybutylene terephthalate oligomer with the most preferred cyclobutarene ketoanhydride monomer will yield an endcapped polyester of the formula:

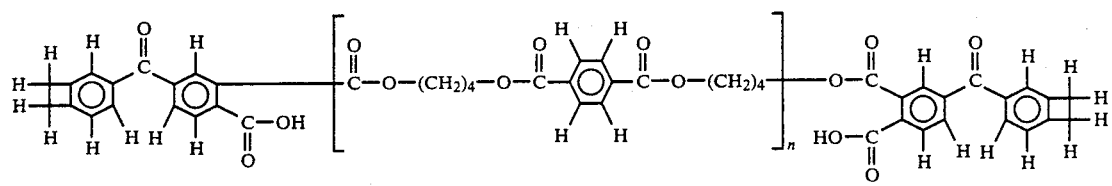

wherein n is an integer from 2 to 4.

mers and includes not only conventional difunctional oligomers sold commercially but also low molecular weight copolymers prepared from the processes of this invention. The term "endcapped" refers to the placement of the cyclobutarene monomers on the oligomer chain in such a way that the oligomer terminates with An endcapped polyamide can be prepared in a like manner. As an example, the endcapping of a polyamide oligomer, preferred from the copolymerization of terephthalic acid and methylene dianiline, with the most preferred cyclobutarene ketoanhydride monomer will yield an endcapped polyamide of the formula:

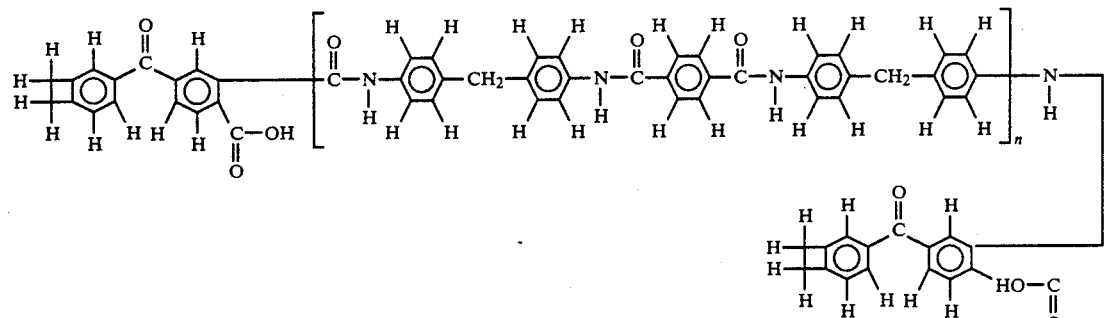

wherein n is an integer from 2 to 4.

the cyclobutarene moieties.

An oligomer that can undergo at least two condensation reactions can be endcapped by subjecting the oligomer and a cyclobutarene monomer of this invention to condensation polymerization conditions similar to those described hereinbefore. However, equimolar amounts of the oligomer and the monomer are neither required nor preferred. Preferably, the amount of monomer em- An endcapped polyimide can also be prepared in a like manner. For example, the endcapping of a polyimide oligomer, prepared from the copolymerization of 1,2,4,5-benzenetetracarboxylic dianhydride and phenylene diamine (sold by DuPont under the trademark KAPTON®), with the most preferred cyclobutarene ketoanhydride monomer will yield an endcapped polyimide of the formula:

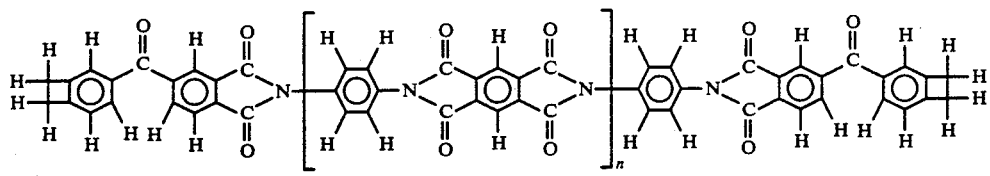

wherein n is an integer from 2 to 4.

Another example of the endcapping of a polyimide oligomer, prepared from the copolymerization of toluenediisocyanate (TDI), methylenedianlineisocyanate (MDI), and 3,4',4,4'-benzophenonetetracarboyxlic acid dianhydride (BTD) (sold by The Dow Chemical Company under the trademark Polyimide ®2080), with the most preferred cyclobutarene ketoanhydride monomer will yield an endcapped polyimide of the formula:

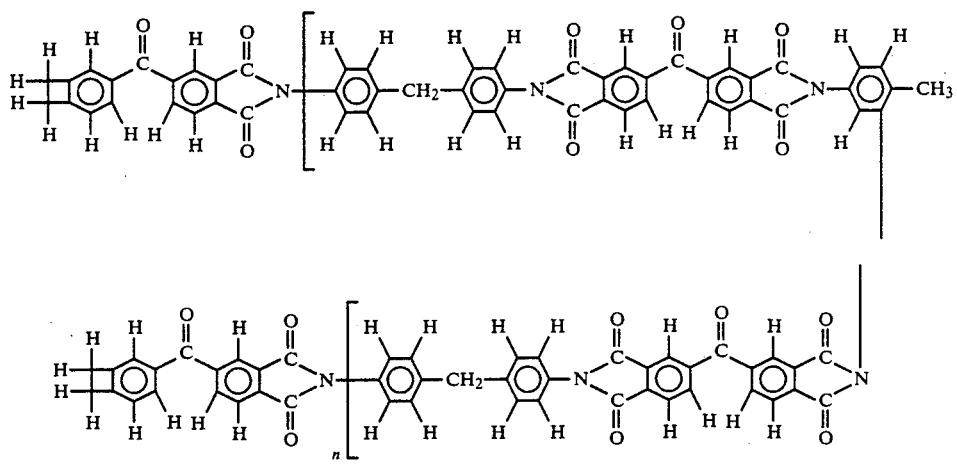

wherein n is an integer from 2 to 4.

The copolymers and the endcapped oligomers of this invention can be subjected to ring scission polymerization conditions to prepare highly crosslinked, three-dimensional polymeric networks. In this context, "ring scission polymerization" refers to the reaction of an opened cyclobutane ring on a cyclobutarene moiety with either another opened cyclobutane ring or a moiety capable of reacting with an opened cyclobutane ring.

When the cyclobutane ring of the cyclobutarene moiety opens, it forms a conjugated diene (orthoquinodimethane) that can react with a dienophilic moiety (a"diene loving" moiety). Unlike condensation polymerization, a small molecule is not split out during the reaction. Typically, the opened ring reacts with another opened ring. U.S. Pat. No. 4,540,763 discloses some of the potential reactions that can occur when opened rings react with each other. An opened ring can potentially react with an olefinic or acetylenic moiety via a Diels-Alder reaction as disclosed in Feiser and Feiser, Organic Chemistry, 3rd ed., 1980.

The cyclobutane ring of the cyclobutarene moiety can open by subjecting the copolymers or the endcapped oligomers of this invention to sufficient heat. Typically, temperatures from about 200° C. to 300° C. are sufficient to open the ring. Polymerization solvents or catalysts are unnecessary, although a copper salt catalyst may lower the required temperature. Gamma radiation and electron beam radiation can also open the ring, but thermal radiation is preferred since it can be applied by conventional methods.

In a similar manner, the cyclobutarene ketoanhydride monomers can be subjected to ring scission polymerization conditions to prepare low molecular weight homopolymers.

The monomeric and polymeric compositions of this invention are useful as thermoset resins that exhibit a wide range of desirable properties for engineering applications. Their mechanical properties, thermal stability at extreme temperatures, and chemical resistance easily make them highly suitable for preparing advanced composites, lamiantes for circuit boards, passivation or planarization resins, and die attach materials. They can be used for any other application where high performance thermoset resins are required.

The following examples are illustrative only and are not intended to limit the scope of this invention.

EXAMPLE 1 - Preparation of 4-Benzocyclobutenyl-4(1,2-Dicarboxylic Acid Anhydro) Phenyl Ketone

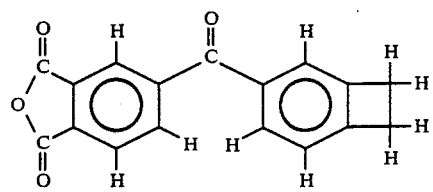

3.0 grams (g) (28.85 mmol) of Benzocyclobutene, 4.07 g (19.23 mmol; 0.67 equivalents per equivalent of benzocyclobutene) of trimellitic anhydride acid chloride and 31 mg (0.193 mmol) of iron (III) oxide are charged to a 25 ml roundbottom flask equipped with a magnetic stirring bar and reflux condenser with a nitrogen inlet. The mixture is vigorously stirred and is heated to 135° C. under a nitrogen atmosphere with the aid of an oil bath. The reaction mixture is maintained at this temperature for 20 hours, and is subsequently cooled to room temperature. The mixture forms a deep red-brown viscous liquid. It is contacted with 100 ml of chloroform and forms a separate organic phase. This organic phase is separated from the residual material in a separatory funnel and is washed with 10 percent sodium bicarbonate (2×50 ml), water (2×50 ml), and saturated sodium chloride (1×50 ml). The washed organic layer is then dried over magnesium sulfate and is filtered through celite. The resulting solution is concentrated on a rotary evaporator and yields a deep red-brown viscous liquid. This viscous liquid is treated with 100 ml of n-hexane and is vigorously agitated for 5 minutes. The hexane is decanted from the viscous liquid and the hexane treatment is repeated 2 more times. DUring the hexane treatments, the material forms a dark yellow solid. This dark yellow solid is then treated with boiling hexane. The hexane is decanted from the mixture and the solid is recrystallized from carbon tetrachloride and a small amount of decolorizing charcoal. 1.5 Grams (28 percent yield) of a bright yellow solid are recovered. This solid has a melting point between 131° and 132° C. The analysis by means of NMR, IR, elemental analysis, mass spectrum and differential scanning calorimetry of the solid is consistent with the structure of 4-benzocyclobutenyl-4(1,2-dicarboxylic acid anhydro) phenyl ketone.

EXAMPLE 2 - Preparation of the Homopolymer of 4-benzocyclobutenyl-b 4(1,2-Dicarboxylic Acid Anhydro) Phenyl Ketone From Example 1

The monomer of Example 1 is heated to approximately 200° C. and displays a polymerization exotherm in a differential scanning calorimeter. The exotherm reaches a maximum temperature of approximately 261° C. After the maximum temperature is reached, the sample is cooled to room temperature and is once again heated to 200° C. The sample now no longer has a melting point and does not exotherm at 200° C. A glass transition temperature exhibited at 149.7° C. indicates the presence of a material with a higher molecular weight than the starting material.

EXAMPLE 3 - Preparation of 4-Benzocyclobutenyl-4(1,2-Dicarboxyli Acid) Phenyl Ketone

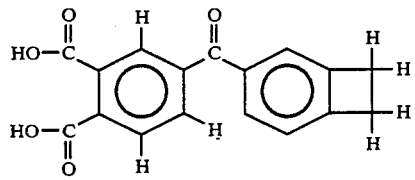

1.3 g (4.67 mmol) of 4-Benzocyclobutenyl-4-(1,2-dicarboxylic acid anhydro) phenyl ketone, 2.0 g (50 mmol) of sodium hydroxy and 20 ml of distilled water are charged to a 50 ml roundbottom flask equipped with a magnetic stirring bar and a reflux condenser with a nitrogen inlet. The reaction mixture is stirred at room temperature under a nitrogen atmosphere for 3 hours and is then heated at gentle reflux for 18 hours. After 18 hours, the reaction mixture is cooled to room temperature and is filtered. The material in the filter funnel is washed with 50 ml of distilled water. The filtrate is acidified with an aqueous solution of 50 percent hydrochloric acid until a pH of 2 is obtained. The white solid which forms is isolated by suction filtration and is dried in a vacuum oven at 80° C. for 18 hours. This solid has a melting point between 140° and 145° C. The infrared spectrum is consistent with the structure of 4-benzocyclobutenyl-4(1,2-dicarboxylic acid) phenyl ketone.

EXAMPLE 4 - Preparation of 4-Benzocyclobutenyl-4(1,2-Diethyldicarboxylato) Phenyl Ketone

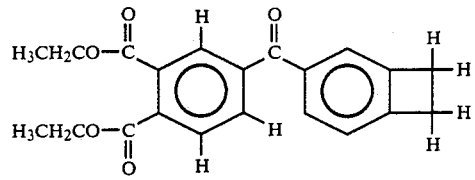

200 mg (0.719 mmol) of 4-Benzocyclobutenyl-4(1,2-dicarboxylic acid anhydro) phenyl ketone in 5.0 ml of ethanol are charged to a 25 ml roundbottom flask equipped with a magnetic stirring bar and reflux condenser. A drying tube using calcium chloride as a desiccant to remove moisture from the air is placed on the top of the reflux condenser. The solution is stirred and 30 mg (0.158 mmol) of paratoluene sulfonic acid is added. The reaction mixture is heated to reflux and is maintained at reflux for 12 hours. After 12 hours, the mixture is cooled to room temperature and forms a viscous liquid. The excess ethanol is removed on a rotary evaporator. The reaction mixture is then dissolved in 50 ml of chloroform and is washed with an aqueous solution of 10 percent sodium bicarbonate (2×20 ml) and distilled water (2×20 ml). The washed reaction mixture is dried over magnesium sulphate and then filtered through celite to remove the magnesium sulphate. The resulting solution is concentrated on a rotary evaporator and yields 115 mg of an oily product. The analysis by means of NMR and IR for the product are consistent within the proposed structure.

Example 5 - Preparation of 4-Benzocyclobutene Capped Imide

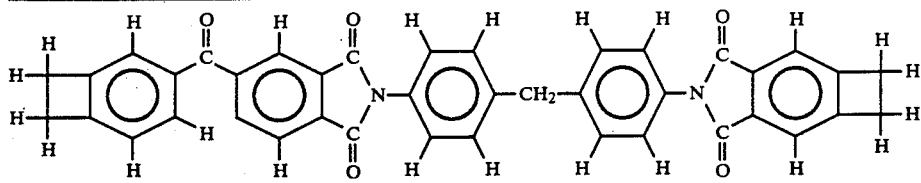

85.4 mg (4.3×10⁻⁴ mol) methylene dianiline is charged to a stirring solution of 0.24 g (8.63×10⁻⁴ mol) of 4-benzocyclobutenyl-4(1,2-dicarboxylic acid anhydro) phenyl ketone and 5.0 ml of acetone at room temperature and under a nitrogen atmosphere. The reaction mixture is stirred for 30 minutes at room temperature and the solvent is subsequently removed on a rotary evaporator. The reaction mixture is then diluted in 10 ml (1.82 g; 0.106 mols) of acetic acid anhydride and is heated to 120° C. After 12 hours at this temperature, the mixture is cooled to room temperature and the acetic anhydride is removed on a rotary evaporator. The resulting brown viscous liquid is dissolved in 5.0 ml of tetrahydrofuran. The dissolved mixture is then added to 100 ml of vigorously stirring distilled water. A yellow flocculant solid forms and is isolated by suction filtration. It is washed with 100 ml of distilled water and is vacuum dried in an oven at 70° C. over night. The weight of the solid after drying is 0.19 g (62 percent yield). The infrared spectrum shows the characteristic imide bands at 1720, 1375, and 725 cm⁻¹. The diphenyl ketone carbonyl is present at 1660 cm⁻¹. The solid appears to melt between 128° and 135° C. on a hot stage microscope melting point structure.

EXAMPLE 6 - Preparation of Highly Crosslinked Network for the Benzocyclobutene Capped Imide of Example 5

A 30 mg sample of the imide obtained from Example 5 is pulverized. The resulting powder is placed on a glass slide and is heated to 250° C. on a hot plate in air. As it is heated, the imide melts and forms a dark amber film. The temperature is maintained at 250° C. for 10 minutes before cooling to room temperature. The film adheres to the surface of the glass and has a hard glossy surface. The film is placed in 1 mol potassium hydroxide for 30 minutes at room temperature and does not dissolve or fall apart. When the film is removed from the potassium hydroxide and rinsed with distilled water it could be removed from the glass surface, yet it still retains its hardness and toughness and does not exhibit any sign of swelling or marring of the polymer. This indicates that the crosslinked polymeric film prepared exhibits good physical properties as well as chemical resistance to a strong base.

What is claimed is:

1. A cyclobutarene of the formula:

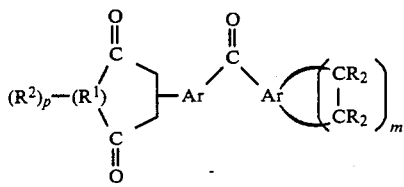

wherein

R is separately and independently in each occurrence a hydrogen atom, an electron donating moiety or an electron withdrawing moiety;

Ar is an aryl moiety or an aryl moiety having atoms other than carbon atoms in its nucleus, which aryl moieties may be substituted with electron-withdrawing substituents or electron-donating substituents; with the proviso that the carbons of the cyclobutene ring connected to the R groups

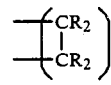

are also bonded to adjacent carbon atoms on the same aromatic ring of Ar;

$R^1$ is an oxygen atom, a nitrogen atom, or a sulphur atom;

$R^2$ is a hydrogen atom, an alkyl moiety having less than 10 carbon atoms, an aryl moiety, or an aryl moiety having atoms other than carbon atoms in its nucleus;

m is an integer of 1 or 2; and p is an integer of zero or 1 provided that p is 1 only when $R^1$ is a nitrogen atom.

2. The monomer of claim 1 of the formula:

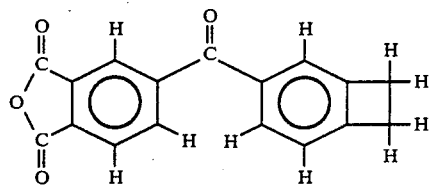

3. A process for preparing the monomer of claim 1 comprising the step of reacting a cyclobutarene with an anhydride-substituted aromatic acid halide in the presence of a reaction catalyst capable of either accepting a pair of electrons or donating a proton during the reaction.

4. The process of claim 3 wherein the acid halide has the formula:

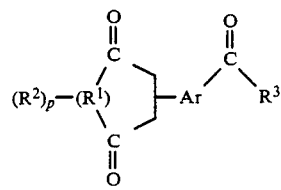

wherein

Ar is an aryl moiety or a heterocyclic moiety;

$R^1$ is an oxygen atom, a nitrogen atom, or a sulphur atom;

R² is a hydrogen atom, an alkyl moiety having less than 10 carbon atoms, an aryl moiety, or a heterocyclic moiety;

R³ is a chlorine atom, bromine atom, or iodine atom; and p is an integer of zero or 1 provided that p is 1 only when R¹ is a nitrogen atom.

5. The process of claim 4 wherien the acid halide is trimellitic anhydride acid chloride.

6. The process of claim 3 wherein the cyclobutarene is benzocyclobutene.

7. The process of claim 3 wherein the reaction catalyst is selected from the group consisting of compounds which function as Lewis acids, strong protic acids and organic complexes of iron and trifluoroacetic anhydride.

8. The process of claim 7 wherein the reaction catalyst is selected from the group consisting of iron metal, iron (III) oxide, and zinc oxide.

9. The process of claim 8 wherein the reaction catalyst is iron (III) oxide.

10. The process of claim 3 wherein the molar ratio of the cyclobutarene to the acid halide is about 5:4 to about 12:4.

11. The process of claim 10 wherein the molar ratio of the cyclobutarene to the acid halide is about 6:4.

12. The process of claim 10 wherein the molar ratio of the acid halide to the reaction catalyst ranges from about 10 to about 500.

13. The process of claim 12 wherein the temperature of the reaction mixture ranges from about 135° C. to about 150° C.

14. The process for preparing a copolymer from the monomer of claim 1 comprising the step of subjecting the monomer of claim 1 and a difunctional monomer that can undergo at least two condensation reactions to condensation polymerization conditions.

15. The process of claim 14 wherein the copolymer prepared is an oligomer.

16. The process of claim 15 wherein the difunctional monomer is selected from the group consisting of primary aromatic diamines, secondary aromatic diamines, saturated aliphatic diols, diphenols, and dithiols.

17. The process of claim 16 wherein the difunctional monomer is selected from the group consisting of methylene dianiline; 1,4-butane diol; bisphenol A; and benzene dithiol.

18. A process for preparing a copolymer from the monomer of claim 2 comprising the step of subjecting the monomer of claim 2 and a difunctional monomer that can undergo at least the condensation reactions to condensation polymerization conditions.

19. A process for preparing oligomers endcapped with a cyclobutarene moiety comprising the step of subjecting an oligomer that can undergo at least two condensation reactions and the monomer of claim 1 to condensation polymerization conditions.

20. The process of claim 19 wherein the oligomer is selected from the group consisting of polyester, polyamide and polyimide oligomers.

21. The process of claim 19 wherein the oligomer is prepared from the process of claim 18.

22. The process of claim 19 wherein the amount of the monomer of claim 1 employed ranges from about 5 mole percent to about 20 mole percent based onthe total molar amount of monomer and oligomer in the reaction mixture.

23. A process for preparing a crosslinked network for the copolymer prepared from the process of claim 14, comprising the step of subjecting the copolymer to ring scission polymerization conditions.

24. A process for preparing a homopolymer from the monomer of claim 1 comprising the step of subjecting the monomer to ring scission polymerization conditions.

* * * * *